United States Patent [19]

Mathieu et al.

[11] Patent Number: 6,087,529
[45] Date of Patent: Jul. 11, 2000

[54] PROCESS FOR THE STABILIZATION OF ALKYLBENZENESULPHONATES

[75] Inventors: Edouard Mathieu, Mont Saint Aignan; Dominique Moulin; Jean Michel Legac, both of N. D. de Gravenchon; Olivier Letailleur, Bolbec, all of France

[73] Assignee: Exxon Chemical Patents Inc., Linden, N.J.

[21] Appl. No.: 09/142,192

[22] PCT Filed: Mar. 10, 1997

[86] PCT No.: PCT/EP97/01263

§ 371 Date: Sep. 1, 1998

§ 102(e) Date: Sep. 1, 1998

[87] PCT Pub. No.: WO97/33864

PCT Pub. Date: Sep. 18, 1997

[30] Foreign Application Priority Data

Mar. 12, 1996 [GB] United Kingdom ............ 9605166
Mar. 12, 1996 [GB] United Kingdom ............ 9605167

[51] Int. Cl.$^7$ .................................. C07C 309/00
[52] U.S. Cl. .................................. 562/96; 562/95
[58] Field of Search ..................... 562/94, 95, 96

[56] References Cited

U.S. PATENT DOCUMENTS

| 2,773,896 | 12/1956 | Putt | 562/94 |
|---|---|---|---|
| 3,367,865 | 2/1968 | Gudells | 562/94 |
| 3,442,965 | 5/1969 | Oldham | 562/94 |
| 3,681,442 | 8/1972 | Bloch et al. | 562/94 |
| 4,235,810 | 11/1980 | Osselet et al. | 562/94 |
| 4,618,458 | 10/1986 | Prillieux et al. | 562/94 |
| 5,344,967 | 9/1994 | Schnur et al. | 562/94 |

*Primary Examiner*—Gary Geist
*Assistant Examiner*—Taylor Victor Oh

[57] ABSTRACT

To improve color and odor characteristics of sulfonic acids and their derivatives while maintaining sludge and sulfuric acid reduction and good thermal stability, they are treated with at least one unsaturated hydrocarbon, each having at most 36 carbon atoms and having defined substitution characteristics.

21 Claims, No Drawings

PROCESS FOR THE STABILIZATION OF ALKYLBENZENESULPHONATES

BACKGROUND OF THE INVENTION

This invention relates to treatments and compositions of sulfonic acids and their derivatives, particularly to sulfonic acids and their derivatives with improved odour and colour characteristics.

Methods and treatments have been proposed which improve the characteristics of sulfonic acids and their derivatives. U.S. Pat. No. 4,153,627 describes sulfonic acids which contain at least 1% by weight of an olefin with improved thermal and colour stability of the acids and reduced sludge and sulfuric acid content. Indeed, the olefins disclosed in above specification U.S. Pat. No. 4,153,627 are derived from propylene and butene oligomers, such as trimers and, tetramers of propylene. EPA-520 808 describes a sulfonic acid treatment with unsaturated hydrocarbon having a number average molecular weight between about 600 and 3000. However, the above specifications do not report the effect of unsaturated hydrocarbon structure on sulfonic acid purification. Furthermore, the above specifications do not disclose the treatment of sulfonic acids and their derivatives with selective types of unsaturated hydrocarbons to resolve problems of odour and colour. In particular, the problem of high $H_2S$ and mercaptan content of the sulfonic acid and their derivatives have not been addressed. High $H_2S$ and mercaptan content give rise to undesirable odour.

It is found, according to this invention, that particular types of unsaturated hydrocarbons can be used to selectively control the colour and odour characteristics of the sulfonic acids and their subsequent derivatives. Thus, one skilled in the art can now improve the colour and odour characteristics of sulfonic acids and their derivatives while maintaining the known advantages of sludge and sulfuric acid reduction and good thermal stability.

SUMMARY OF THE INVENTION

This invention relates to methods of treatment and compositions of sulfonic acids of selective characteristics comprising contacting the sulfonic acid with: at least one unsaturated hydrocarbon selected from at least one of (A), (B), (C) or (D) each having at most 36 carbon atoms, where (A) has at least one carbon to carbon double or triple bond, the carbon atoms bonded by said bond being unsubstituted or being substituted with one hydrocarbyl group in total;

(B) has at least one carbon or carbon double or triple bond, the carbon atoms bonded by said bond being substituted with two hydrocarbyl groups in total;

(C) has at least one carbon to carbon double bond, the carbon atoms bonded by said bond being substituted with three hydrocarbyl groups in total; and (D) has at least one carbon to carbon double bond, the carbon atoms bonded by said bond being substituted with four hydrocarbyl groups in total; with the proviso that if (B), (C) and (D) together are used then at least one thereof has from 2 to 8 carbon atoms or from 25 to 36 carbon atoms.

An advantage of this invention is the flexibility provided in controlling the odour and colour characteristics of the resulting sulfonic acid or sulfonic acid derivative by treating the sulfonic acid with the unsaturated hydrocarbon while maintaining sludge and sulfuric acid reduction and good thermal stability. Indeed, by varying the ratio of at least two of (A), (B), (C) or (D), the odour and colour characteristics of the sulfonic acid may be controlled.

A further aspect of the present invention is, therefore, a process for improving the odour of a sulfonic acid comprising contacting the sulfonic acid with at least one of (A) or (B).

DETAILED DESCRIPTION OF THE INVENTION

Sulfonic Acids

The techniques of the present invention may be applied to a wide variety of sulfonic acids including aliphatic and alkylaryl sulfonic acids obtained by any sulfonation process. They are however primarily directed at the purification of sulfonic acids which contain more than 1 wt. %, particularly those containing more than 2 wt. % of sulfuric acid.

Examples of suitable aliphatic sulfonic acids are those which contain from 7 to 80 carbon atoms, such as described in U.S. Pat. No. 3,629,109.

Examples of alkylaryl sulfonic acid include acids derived from alkylated mono- or poly-nuclear aromatic compounds known as alkylates. The invention is primarily concerned with sulfonic acids derived from mono-nuclear aromatic compounds; the aromatic nucleus may contain the single alkyl group as in the alkyl benzenes or two alkyl groups such as in the alkyl toluenes or the dialkyl benzenes or three alkyl groups such as for example in the alkyl xylenes. Thus the sulfonic acid may be of the formula:

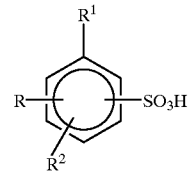

where one or both of $R^1$ and $R^2$ may be hydrogen or hydrocarbyl groups and R is an alkyl group which contains 7 to 100, preferably 16 to 60+ such as 80 carbon atoms and may be straight or branched chain. Although the techniques of the invention are applicable to sulfonic acids in which R is a comparatively short chain alkyl group such as from $C_7$ to $C_{15}$, the techniques prove especially useful with the sulfonic acids in which R is a longer chain such as from $C_{16}$ to $C_{80}$ which require special purification techniques. The techniques of the invention are found to be particularly suited to the production of sulfonic acids based on alkyl aryl compounds in which the alkyl group contains from 16 to 80 carbon atoms or from 12 to 40 carbon atoms.

Suitable sulfonation techniques include treatment with oleum (fuming sulfuric acid), or with chloro sulfuric acid, and direct $SO_3$/air or $SO_2/SO_3$ sulfonation. Direct $SO_2/SO_3$ sulfonation is preferred.

A sulfonic acid should contain no more than 0.5 wt. % sulfuric acid to be commercially acceptable, which is generally achievable by treatment with an unsaturated hydrocarbon provided the acid contains no more than 3 wt. %, preferably 2 wt. % of sulfuric acid prior to treatment. Also, it is desirable that the odour of the sulfonic acid and its derivatives be minimised, that its colour be water-white, and it should be thermally stable under normal storage conditions.

Unsaturated Hydrocarbons

Preferred unsaturated hydrocarbons, whether (A), (B), (C) or (D) or a mixture thereof with the proviso that the mixture is not (B), (C) and (D), for use in this invention have at most 24 carbon atoms, more preferably at most 15, most preferably at most 12, especially at most 9, and more especially at most 8 carbon atoms.

Preferred unsaturated hydrocarbons, of (A) or (B) or both for use in this invention have from 2 to 24 carbon atoms, more preferably 2 to 15, most preferably 2 to 12, especially 2 to 9 and more especially 2 to 8 carbon atoms.

Preferred unsaturated hydrocarbons of (C) or (D) or both for use in this invention have from 5 to 24 carbon atoms, more preferably 2 to 15, most preferably 2 to 12, especially 2 to 9 and more especially 2 to 8 carbon atoms.

A preferred unsaturated hydrocarbon comprises (A), (B), (C) and (D) for treating a sulfonic acid.

Furthermore, it is found that unsaturated hydrocarbons having at most 15, preferably at most 12, more preferably at most 9 and most preferably at most 8 carbon atoms may be removed from the sulfonic acid by physical methods and under conditions that do not damage the sulfonic acid in any way, for example by causing it to decompose. Examples of removable unsaturated hydrocarbons are those that are sufficiently volatile to be strippable from the sulfonic acid without causing damage thereto.

In the instance where (B), (C) and (D) together are used to treat the sulfonic acid, it is preferred that at least one of (B), (C) or (D) has from 2 to 8 carbon atoms, more preferably at least two has from 2 to 8 carbon atoms, most preferably each of (B), (C) and (D) has from 2 to 8 carbon atoms.

The unsaturated hydrocarbon for use in this invention may have multiple carbon to carbon double or triple bonds, but it is preferred that the unsaturated hydrocarbon has only one carbon to carbon double or triple bond, more preferably the unsaturated hydrocarbon, whether (A), (B), (C) or (D) or a mixture thereof or both, is a mono-olefin, that it has one carbon to carbon double bond, and that any remaining valencies of said double bonded carbon atoms are satisfied by hydrogen atoms.

As used in this specification the term 'removable' refers to unsaturated hydrocarbons which can be removed form the sulfonic acid by physical methods and under conditions that do not damage the sulfonic acid in any way, for example by causing it to decompose.

As used in this specification the term "hydrocarbyl" refers to a group having a carbon atom directly attached to the rest of the molecule and having a hydrocarbon or predominantly hydrocarbon character. Among these, there may be mentioned hydrocarbon groups, including aliphatic, (e.g. alkyl), alicylic (e.g., cycloalkyl), aromatic, aliphatic and alicylic-substituted aromatic, and aromatic-substituted aliphatic and alicyclic groups. Aliphatic groups are advantageously saturated. These groups may contain non-hydrocarbon substituents provided their presence does not alter the predominantly hydrocarbon character of the group. Examples include keto, halo, hydroxy, nitro, cyano, alkoxy and acyl. If the hydrocarbyl group is substituted, a single (mono) substituent is preferred. Examples of substituted hydrocarbyl groups include 2-hydroxyethyl, 3-hydroxypropyl, 4-hydroxybutyl, 2-ketopropyl, ethoxyethyl, and propoxypropyl. The groups may also or alternatively contain atoms other than carbon in a chain or ring otherwise composed of carbon atoms. Suitable hetero atoms include, for example, nitrogen, sulfur, and, preferably, oxygen. Advantageously, the hydrocarbyl group contains at most 30, preferably at most 15, more preferably at most 10 and most preferably at most 8 carbon atoms. Preferred hydrocarbyl groups are alkyl groups, which may be straight chain or branched and may be primary, secondary or tertiary.

Examples of unsaturated hydrocarbons (A) having one (1) hydrocarbyl substitution are $C_2$ to $C_{36}$ alpha-olefins. The term alpha-olefin means that the double bond is between the first and second carbon atoms of the unsaturated hydrocarbon. The unsaturated hydrocarbon (A) encompasses ethene and ethyne.

Specific examples of alpha-olefins are 1-propene, 1-butene, 1-pentene, 1-hexene, 1-heptene, 1-octene, 1-nonene, 1-decene, 1-undecene, 1-dodecene, 1-hexadecene, 1-heptadecene, 1-octadecene, 1-nonadecene, 1-eicosene, 1-hexeicosene, 1-docosene, 1-tetracosene, 1-pentacosene, 1-hexacosene, 1-octacosene, and 1-nanocosene, including mixtures thereof such as commercially available mixtures.

Examples of unsaturated hydrocarbons (B), i.e. having two (2) hydrocarbyl substitution, are $C_4$ to $C_{36}$ cis/trans-olefins and $C_4$ to $C_{36}$ vinyldenic olefins. The term cis-olefin means that there is one (1) hydrocarbyl substitution on each of the carbon atoms bonded by the double bond which are stereochemically arranged on the same side of the double bond. The term trans-olefin signifies that there is one (1) hydrocarbyl substitution on each of the carbon atoms bonded by the double bond which are stereochemically arranged on the opposite sides of double bond. An example of a cis/trans olefin is 2-pentene. Vinyldenic olefins are olefins in which the two (2) hydrocarbyl substitutions are on the same carbon atom of the carbon atoms bonded by the double bond, an example of which is 2-methyl-1-propene.

Examples of unsaturated hydrocarbons (C) having three (3) hydrocarbyl substitutions are $C_5$ to $C_{36}$ tri-substituted olefins such as 3-methyl-2-butene and 3-methyl-2-pentene.

Examples of unsaturated hydrocarbons (D) having four (4) hydrocarbyl substitutions are tetra-substituted olefins, that is olefins where each carbon atom bonded by the double-bond carries two (2) hydrocarbyl groups, such as 2,3-dimethyl-2-butene.

It will be appreciated by one skilled in the art that it is possible to have unsaturated hydrocarbons which, in a single composition, contain mixtures of unsaturated hydrocarbons (A), (B), (C) or (D), or mixtures thereof. Examples of such include $C_6$ to $C_{36}$ propylene and butene oligomers. When at least two of (A), (B), (C) or (D) are used, the weight to weight ratio of any one of (A), (B), (C) and (D) to any other of (A), (B), (C) and (D) may, for example, be in the range of from 10:1 to 1:10, preferably 5:1 to 1:5, more preferably 2:1 to 1:2.

Sulfonic Acid Treatment

The sulfonic acid may be treated with the unsaturated hydrocarbons under any number of conditions which are effective to achieve the benefits of this invention. Examples of suitable sulfonation processes may be found in U.S. Pat. No. 4,153,627 and U.S. Pat. No. 4,618,458. While the sulfonic acid can be treated by incorporating the unsaturated hydrocarbon at any stage of the sulfonation process, preferably it is incorporated after sulfonation since incorporation before or during sulfonation tends to reduce the yield of desired sulfonic acid. Also, it is found that if the unsaturated hydrocarbon is present during removal of the sulfur dioxide when the alkylaryl compound has been sulfonated with a solution of sulfur trioxide in sulfur dioxide then the amount of sludge that remains after removal of the sulfur dioxide is considerably reduced as is the amount of sulfuric acid. It is found in certain instances that the reduction in sludge and sulfuric acid, even in the production of sulfonic acids based on the longer chain alkylates, is sufficient that it may not be necessary to remove sludge by decanting with a hydrocarbon solvent or to wash with aqueous hydrochloric acid solution to remove sulfuric acid. As can be seen this would lead to a considerable simplification of the process for manufacturing sulfonic acids. It is also found that within normal operating limits the temperature at which the unsaturated hydrocarbon is mixed with the sulfonic acid is not critical.

It is further found that when sulfonation is effected with sulfur trioxide dissolved in sulfur dioxide the need for purifying the sulfonic acid so produced can be obviated if, after sulfonation, the sulfur dioxide is removed while an unsaturated hydrocarbon is present. Thus, in one further aspect, the present invention provides a process for stabilising an alkylaryl sulfonic acid which has been prepared by sulfonating an alkylaryl hydrocarbon with sulfur trioxide dissolved in sulfur dioxide and wherein the sulfur dioxide is removed after sulfonation, characterised by removing at least part of the sulfur dioxide while the product of sulfonation contains at least 1% by weight of an unsaturated hydrocarbon based on the weight of alkylate charge.

Where a removable unsaturated hydrocarbon is added prior to or during removal of the sulfur dioxide, it may be sufficiently volatile to be removed with the sulfur dioxide. Thus, in this instance, more unsaturated hydrocarbon will be required to treat the sulfonic acid than if unsaturated hydrocarbon treatment occurs after a major portion of the sulfur dioxide is removed. Thus, a preferred method is to add the removable unsaturated hydrocarbon immediately after a major portion of the sulfur dioxide has been removed from the sulfonic acid. In this way, the benefits of improved odour can be taken advantage of before the sulfonic acid is stored or derivativised.

In the instance where the unsaturated hydrocarbon may not be sufficiently volatile to be removed with the sulfur dioxide, a preferred method is to add the unsaturated hydrocarbon immediately after making the sulfonic acid so that the benefits of improved odour can be taken advantage of before the acid is stored or derivatised.

It is found that selective treatment of sulfonic acids with the unsaturated hydrocarbon (A) or (B) or (A) and (B) produces sulfonic acids with lower levels of $H_2S$ and little, if no, mercaptan emission. These benefits result in lessened or eliminated odour problems which is desired to be minimised to prevent objectionable smells during processing and further handling.

Selective treatment of sulfonic acids with the unsaturated hydrocarbon (C) or (D) or (C) and (D) produces sulfonic acids of low colour. Therefore, both the odour and colour of the sulfonic acid may be adjusted accordingly by varying the relative amounts of the unsaturated hydrocarbons (A), (B), (C) and/or (D).

At least 1% of unsaturated hydrocarbon by weight of the alkylate charge from which the sulfonic acid is derived is then added to the sulfonic acid. For economic and product stability reasons it is preferred to use as little unsaturated hydrocarbon as possible, preferably less than 10%; at least 1% by weight should be used, and it is preferred to use from 2% to 10% by weight, more preferably from 3% to 6% by weight. However, it will be appreciated by one skilled in the art that there may be other suitable amounts outside the foregoing ranges where the benefits of this invention are achieved. Indeed, the removable unsaturated hydrocarbon can be used freely without concern for sulfonic acid product stability because any free unsaturated hydrocarbon is removed such as by stripping.

In the treated sulphonic acid, or sulphonate derived therefrom, the unsaturated hydrocarbon may not necessarily be present as free unsaturated hydrocarbon, but at least partly in a reacted form. A further aspect of the invention is a sulphonic acid or sulphonate salt containing at least 1% by weight, preferably at least 0.05%, of unsaturated hydrocarbon, where the unsaturated hydrocarbon is as defined herein. In this aspect of the invention, (A), (B), (C) and/or (D) may be present either as such or in a reacted form or as both.

Where the unsaturated hydrocarbon is selected from two of (A), (B), (C) or (D) to treat the sulfonic acid, it will be appreciated by one skilled in the art that they may be added sequentially, for example (A) then (B) or (B) then (A), or added as a mixture, or added contemporaneously. It is preferred that the unsaturated hydrocarbon be added as a mixture.

The water treatment described in U.S. Pat. No. 4,153,627, the water treatment followed by final heat treatment described in U.S. Pat. No. 4,618,458, and the gaseous treatment described in EP-A-0,520,808, may, if desired, be applied in the practice of the present invention.

Sulfonic Acid Derivatives

Sulfonic acids are generally neutralised to give sulfonates that are used as detergents where they are generally used as their salts with alkali metals such as lithium, potassium, and sodium, or alkaline earth metals such as magnesium, calcium and barium; or with quarternary nitrogenous cations. Sulfonic acids are also used in the production of low basic sulfonates or highly basic sulfonates of the type that are used as detergent additives in lubricating oils. In this instance, the sulfonates are normally lithium, potassium, sodium, calcium, magnesium, or barium salts. Sulfonates may be used as emulsifiers in the formation of oil-in-water emulsions as for example in lubricating oils for metal working, the sulfonates usually being the potassium, sodium or ammonium salts including ethoxylated ammonium salts.

Sulfonates are produced by neutralisation of the sulfonic acids and thus the present invention further provides a process for the production of sulfonates from sulfonic acids produced according to the present invention.

The treated sulfonic acids and their derivatives are generally supplied as concentrates. The concentrates preferably contain from 50% to 95% by weight usually 65% to 90% by weight of the sulfonic acid or derivative in any suitable diluent, for example diluent oil or solvent.

When used in a lubricating oil, the derivatised sulfonic acid may be combined with any number of known lubricating oil additives and a major portion of lubricity oil. Examples of such additives include antiwear agents such as zinc salts of dialkyldithio phosphates; ashless dispersants such as hydrocarbyl substituted succinimides; ashless and metal containing antioxidants; viscosity index improvers; and pour point depressants.

Thus, another aspect of the invention is an oil composition comprising a major proportion of lubricating oil and a minor proportion, admixed therewith, of the derivatised sulfonic acid or sulfonate.

The lubricating compositions and concentrates of this invention comprise defined components that may or may not remain the same chemically before and after mixing with a lubricating oil or with any known lubricating oil additives.

A further aspect of the invention is a sulphonic acid or sulphonate containing at least 0.05% by weight of unsaturated hydrocarbon as defined herein, less than 0.5% by weight of sulphuric acid and less than 10 mole %, preferably less than 5 mole %, of hydrogen sulphide as measured by gas chromatography.

The present invention is illustrated by but in no way limited to the following examples.

EXAMPLES

The following general procedure was utilized to demonstrate this invention. The particular samples prepared and analysed are summarized in Tables 1 to 5.

A $C_{16}$ to $C_{60+}$ or $C_{12}$ to $C_{30+}$ alkyl benzene (alkylate) was sulfonated with a $SO_3/SO_2$ mixture under atmospheric conditions and a temperature of $-10°$ C.

The resulting sulfonic acid was warmed to 0° C. in order to remove $SO_2$. At this stage, a particular treat amount of unsaturated hydrocarbon based on mass % of alkylate was added to the sulfonic acid. The resulting mixture was then heated to 130° C. Any remaining $SO_2$ and any remaining removable unsaturated hydrocarbon, if used, were then purged from the mixture firstly at atmospheric pressure and then under vacuum. The sulfonic acid was cooled to below 50° C. for storage.

The treated sulfonic acid samples were then analysed for colour and odour characteristics. The sulfonic acid was converted to its sodium salt and the colour determined by ASTM D1500 based on 7% by mass in white oil. According to this method a colour characteristic of zero ("0") refers to a water-white liquid. Thus, lower colour values are indicative of paler liquids.

The odour characteristics were measured by determining the presence of $H_2S$ and mercaptans in the vapour phase of the sample by gas chromatography, where the gas chromatograph was fitted with a sulphur-chemiluminescence detector (manufactured by Sievers Instruments), for example as described in "International Chromatography Laboratory: vol 19, ps 4–8, April 1994" by Dr. R. Shearer. The specific procedure followed to determine the vapour phase $H_2S$/mercaptan composition consisted of the following steps: (1) a 100 g sulfonic acid sample was placed and sealed into a 250 cc bottle; (2) the bottle was stored for 14 days under a controlled temperature of 60° C.; (3) the bottle was then warmed to 130° C. for 1 hour; (4) the bottle was vigorously shaken to create equilibrium between the vapor and liquid phases of the sulfonic acid; (5) a sample of the vapor phase was extracted with a syringe from the bottle and was injected into the gas chromatograph for analysis.

TABLE 1

(Treatment of $C_{12}$–$C_{30+}$ Sulfonic Acids)

|  | 1 | 2 | 3 | 4 | 5 |
|---|---|---|---|---|---|
| EXAMPLE |  |  |  |  |  |
| UNSATURATED HYDROCARBON[1] | n-$C_3$ | n-$C_3$ | n-$C_3$ | $C_3$ | $C_3$ |
| DOUBLE BOND C-SUBSTITUTION | 1 | 1 | 1 | 1 | 1 |
| MASS % UNSAT. HYDROCARBON[2] INITIAL ANALYSIS: | 2 | 8 | 9 | 13.5 | 15 |
| MASS % $H_2SO_4$ | 0.6 | 0.66 | 0.35 | 0.33 | 0.43 |
| COLOUR | 35 | 2.5 | 2.5 | 1.5 | 2.5 |

NOTES
[1]=n-$C_3$ = 1-propene.
[2]:Mass % unsaturated hydrocarbon based on alkylate.

Referring to Table 1, examples 1–5 demonstrate the effects of varying amounts of unsaturated hydrocarbon (A) (for example n-$C_3$) on $H_2SO_4$ content and the colour characteristics of a $C_{12}$–$C_{30+}$ sulfonic acid. Specifically, one observes that in general, low-treat rates of n-$C_3$ gives poor colour characteristics (Ex. 1, colour=3.5) but that the colour characteristics generally improve by increasing the amount of n-$C_3$ (i.e., providing excess amounts of strippable unsaturated hydrocarbon, see e.g., Ex. 4, colour=1.5; Ex. 5, colour=2.5). The general trend of increasing the treat amount of strippable unsaturated hydrocarbon supports colour improvement.

Referring to Table 2, examples 6–8 demonstrate the effects of an unsaturated hydrocarbon (A) having 18 carbon on a $C_{16}$–$C_{60+}$ sulfonic acid. Specifically, one observes low $H_2S$ and mercaptan levels. At a treat rate of 3 mass % of n-$C_{18}$, the colour values range from 5 to 5.5 as shown in Examples 6 and 7. However, the colour characteristics may be improved by increasing the treat rate to 5 mass % as shown in Example 8 while maintaining low $H_2S$ and mercaptan levels.

TABLE 2

Treatment of $C_{16}$–$C_{60+}$ Sulfonic Acids)

|  | 6 | 7 | 8 |
|---|---|---|---|
| EXAMPLE |  |  |  |
| UNSATURATED HYDROCARBON[1] | n-$C_{18}$ | n-$C_{18}$ | n-$C_{18}$ |

TABLE 2-continued

Treatment of $C_{16}$–$C_{60+}$ Sulfonic Acids)

|  | 6 | 7 | 8 |
|---|---|---|---|
| DOUBLE BOND C-SUBSTITUTION | 1 | 1 | 1 |
| MASS % UNSAT. HYDROCARBON[2] INITIAL ANALYSIS: | 3 | 3 | 5 |
| MASS % $H_2SO_4$ | 0.1 | 0.13 | 0.08 |
| COLOUR | 5 | 5.5 | 3 |
| 14 DAY CONCENTRATE STABILITY @60° C.: |  |  |  |
| $H_2S$ LEVEL[3] | 3.327 | 1.919 | 3.863 |
| $SO_2$ LEVEL[3] | 96.673 | 98.081 | 96.137 |
| MERCAPTAN LEVEL[3] |  |  |  |
| $CH_3SH$ | <0.001 | <0.001 | <0.001 |
| $C_2H_5SH$ | <0.001 | <0.001 | <0.001 |
| $(CH_3)_2CHSH$ | <0.001 | <0.001 | <0.001 |
| $nC_3H_7SH$ | <0.001 | <0.001 | <0.001 |
| $C_2H_5(CH_3)CHSH$ | <0.001 | <0.001 | <0.001 |
| $nC_4H_9SH$ | <0.001 | <0.001 | <0.001 |

NOTES
[1]=n-$C_{18}$ = normal octadecene:
[2]:Mass % unsat. hydrocarbon based on alkylate charge.
[3]:Based on S mol %.

TABLE 3

Treatment of $C_{12}$–$C_{30+}$ Sulfonic Acids)

|  | 9 | 10 | 11 | 12 |
|---|---|---|---|---|
| EXAMPLE |  |  |  |  |
| UNSATURATED HYDROCARBON[1] | n-$C_3$ | n-$C_5$ | n-$C_5$ | sub-$C_5$ |
| DOUBLE BOND C SUBSTITUTION | 1 | 1 | 1 | 3 |
| MASS % UNSAT. HYDROCARBON[2] INITIAL ANALYSIS: | 3 | 2 | 2.7 | 2.7 |
| MASS % $H_2SO_4$ | 0.6 | 0.41 | 0.14 | 0.10 |
| COLOUR | 3.5 | 3 | 2 | 1 |
| 14 DAY CONCENTRATE STABILITY @60° C.: |  |  |  |  |
| $H_2S$ LEVEL[3] | 0.486% | low | low | high |
| $SO_2$ LEVEL[3] | 99.514 | — | — | — |
| MERCAPTAN LEVEL[3] | none | none | none | yes |
| $CH_3SH$ | <0.001 |  |  |  |
| $C_2H_5SH$ | <0.001 |  |  |  |
| $(CH_3)_2CHSH$ | <0.001 |  |  |  |
| $nC_3H_7SH$ | <0.001 |  |  |  |
| $C_2H_5(CH_3)CHSH$ | <0.001 |  |  |  |
| $nC_4H_9SH$ | <0.001 |  |  |  |

NOTES
[1]=n-$C_3$ = 1-propene;
  n-$C_5$ = 1-pentene;
  sub-$C_5$ = 2-methyl-2-butene (isoamylene);
[2]:Mass % unsaturated hydrocarbon based on alkylate.
[3]:Based on S mol %.

Referring to Table 3, examples 10 to 12 were not evaluated by the gas chromatography technique hereinbefore described. However, the products of Examples 10 and 11 were perceived by smell to have little odour, whereas the product of Example 12 was perceived by smell to be malodorous. Examples 9–12 demonstrate the effects of varying amount and type of carbon substitution of unsaturated hydrocarbon on the odour and the colour characteristics of treated $C_{12}$–$C_{30+}$ sulfonic acid. In particular, Example 9 (one hydrocarbyl substitution—an example of hydrocarbon (A)) shows low $H_2S$ levels and no measurable mercaptan emission. Example 12 (three carbon substitution—an example of hydrocarbon (C)) was malodorous. Comparison between Examples 10 and 11 show that improved colour characteristics can be obtained for unsaturated hydrocarbon (A) by increasing the treat amount of the unsaturated hydrocarbon.

TABLE 5

Treatment of $C_{16}$–$C_{60+}$ Sulfonic Acids)

| EXAMPLE | A | B | C |
|---|---|---|---|
| UNSATURATED HYDROCARBON[1] | tert-$C_{12}$ | $C_{24}$ | $C_{36}$ |
| DOUBLE BOND C-SUBSTITUTION | 2–4 | 2–4 | 2–4 |
| MASS % UNSAT. | 3 | 3 | 5 |

TABLE 4

Treatment of $C_{16}$–$C_{60+}$ Sulfonic Acids)

| EXAMPLE | 13 | 14 | 15 | 16 | 17 | 18 | 19 | 20 | 21 |
|---|---|---|---|---|---|---|---|---|---|
| UNSATURATED HYDROCARBON[1] | n-$C_3$ | sub-$C_4$ | n-$C_5$ | c/t-$C_5$ | sub-$C_5$ | sub-$C_5$ | n-$C_6$ | sub-$C_6$ | sub-$C_6$ |
| DOUBLE BOND C-SUBSTITUTION | 1 | 2 | 1 | 2 | 3 | 3 | 1 | 3 | 4 |
| MASS % UNSAT. | 8 | 3 | 4 | 4 | 4 | 3 | 3 | 4 | 4 |
| HYDROCARBON[2] INITIAL ANALYSIS: | | | | | | | | | |
| MASS % $H_2SO_4$ | 1.08 | 0.46 | 0.13 | 0.41 | 0.1 | 0.19 | 0.3 | 0.08 | 0.12 |
| COLOUR | 4 | 2.5 | 3 | 2.5 | 1.5 | 2 | 3 | 1.5 | 1.5 |
| 14 DAY CONCENTRATE STABILITY @60° C.: | | | | | | | | | |
| $H_2S$ LEVEL[3] | 0.083 | 0.873 | 1.886 | 0.702 | 15.527 | 9.148 | 0.997 | 27.683 | 21.919 |
| $SO_2$ LEVEL[3] | 99.917 | 99.077 | 98.114 | 99.298 | 83.347 | 90.422 | 99.003 | 66.234 | 74.274 |
| MERCAPTAN LEVEL[3] | | | | | | | | | |
| $CH_3SH$ | <0.001 | <0.001 | <0.001 | <0.001 | <0.001 | <0.001 | <0.001 | 0.051 | 0.083 |
| $C_2H_5SH$ | <0.001 | <0.001 | <0.001 | <0.001 | <0.001 | 0.140 | <0.001 | 0.356 | <0.001 |
| $(CH_3)_2CHSH$ | <0.001 | 0.03 | <0.001 | <0.001 | 0.034 | <0.001 | <0.001 | 0.329 | 0.238 |
| $nC_3H_7SH$ | <0.001 | 0.02 | <0.001 | <0.001 | 0.708 | 0.1396 | <0.001 | 4.305 | 3.200 |
| $C_2H_5(CH_3)CHSH$ | <0.001 | <0.001 | <0.001 | <0.001 | 0.050 | <0.001 | <0.001 | 0.098 | 0.012 |
| $nC_4H_9SH$ | <0.001 | <0.001 | <0.001 | <0.001 | 0.334 | 0.149 | <0.001 | 0.944 | 0.274 |

NOTES
[1]=n-$C_3$ = 1-propene;
 sub-$C_4$ = 2-methyl-1-propene;
 n-$C_5$ = 1-pentene;
 c-t-$C_5$ = cis/trans 2-pentene;
 sub-$C_5$ = 2-methyl-2-butene (isoamylene);
 n-$C_6$ = 1-hexene;
 sub-$C_6$ = Example 17 = 3-methyl-2-pentene
  Example 18 = 2,3-dimethyl-2-butene;
[2]:Mass % unsaturated hydrocarbon based on alkylate.
[3]:Based on S mol %.

Referring to Table 4, examples 13–21 further demonstrate the benefits of treating a $C_{16}$ to $C_{60+}$ sulfonic acid with unsaturated hydrocarbons. Examples 13 to 16 and 19 are examples of unsaturated hydrocarbons (A) and (B). These examples show low $H_2S$ and mercaptan levels. Examples 17, 18, 20 and 21 demonstrate that use of unsaturated hydrocarbons (C) and (D) which gave high $H_2S$ and mercaptan levels. Also the unsaturated hydrocarbon (C) or (D) gave better colour characteristics ranging from 1.5 to 2 while the hydrocarbons (A) or (B) gave products with higher colour characteristics which range from 2.5 to 4.

TABLE 5-continued

Treatment of $C_{16}$–$C_{60+}$ Sulfonic Acids)

| | A | B | C |
|---|---|---|---|
| HYDROCARBON[2] INITIAL ANALYSIS: | | | |
| MASS % $H_2SO_4$ | 0.05 | 0.08 | 0.02 |
| COLOUR | 2 | 3 | 2.5 |

TABLE 5-continued

Treatment of $C_{16}$–$C_{60+}$ Sulfonic Acids)

|  | A | B | C |
|---|---|---|---|
| 14 DAY CONCENTRATE STABILITY @60° C.: | | | |
| $H_2S$ LEVEL[3] | 26.421 | 20.366 | 14.671 |
| $SO_2$ LEVEL[3] | 73.156 | 79.486 | 85.137 |
| MERCAPTAN LEVEL[3] | | | |
| $CH_3SH$ | <0.001 | 0.026 | <0.001 |
| $C_2H_5SH$ | 0.051 | <0.001 | 0.008 |
| $(CH_3)_2CHSH$ | 0.045 | 0.014 | 0.134 |
| $nC_3H_7SH$ | 0.279 | 0.079 | <0.001 |
| $C_2H_5(CH_3)CHSH$ | <0.001 | 0.003 | 0.05 |
| $nC_4H_9SH$ | 0.048 | 0.026 | <0.001 |

NOTES
[1]=tert-$C_{12}$ = tetramer of 1-propene;
$C_{24}$ = octamer of 1-propene (average number);
$C_{36}$ = nonamer of 1-butene (average number).
[2]:Mass % unsaturated hydrocarbon based on alkylate charge.
[3]:Based on S mol %.

Whilst Table 5 containing the comparative Examples A to C demonstrate the effects of unsaturated hydrocarbons averaging 2 to 4 hydrocarbyl substitutions on the carbon atoms bonded by the double bond (a proportion of (B), (C) and (D)), such unsaturated hydrocarbons are derived from propylene and butene oligomers. Examples A to C exhibit poor odour and acceptable colour characteristics.

Thus, from the foregoing data, one can observe that treatment of sulfonic acid with the unsaturated hydrocarbons (A) and/or (B) give reduced $H_2S$ and mercaptan levels and therefore, improved odour characteristics compared with the second unsaturated hydrocarbons (C) and/or (D). Also, one observes that the unsaturated hydrocarbons (C) and/or (D) give improved colour characteristics compared with the unsaturated hydrocarbons (A) and/or (B). Therefore, one would expect selective combinations of (A), (B), (C) and (D) unsaturated hydrocarbons to give one skilled in the art the flexibility of tailoring the colour and odour characteristics of the treated sulfonic acids. Also, one skilled in the art will appreciate the added flexibility in adding excess amounts of the removable unsaturated hydrocarbons since the condition of removal will ensure that no excess remains in the treated sulfonic acid or metal salt therefore, which enhances product stability.

What is claimed is:

1. A process for improving the odour of a sulfonic acid comprising contacting the sulfonic acid with at least one unsaturated hydrocarbon selected from at least one of (A), (B), (C) or (D), where
   (A) has at least one carbon to carbon double bond, the carbon atoms bonded by said bond being unsubstituted or being substituted with one hydrocarbyl group in total;
   (B) has at least one carbon to carbon double bond, the carbon atoms bonded by said bond being substituted with two hydrocarbyl groups in total;
   (C) has at least one carbon to carbon double bond, the carbon atoms bonded by said bond being substituted with three hydrocarbyl groups in total; and
   (D) has at least one carbon to carbon double bond, the carbon atoms bonded by said bond being substituted with four hydrocarbyl groups in total;
   wherein each of (A), (B), (C) and (D) has from 2 to 8 carbon atoms.

2. The process of claim 1 where the sulfonic acid is contacted with (A), (B), (C) and (D).

3. The process of claim 1 where, when at least two of (A), (B), (C) or (D) are used, the ratio of any one of (A), (B), (C) and (D) to any other of (A), (B), (C) and (D) is in the range of from 10:1 to 1:10 by weight.

4. The process of claim 1 where the sulfonic acid is an alkyl benzene sulfonic acid in which the alkyl group has from 7 to 100 carbon atoms.

5. The process of claim 4 where the sulfonic acid has an alkyl group of from 16 to 80 carbon atoms.

6. The process of claim 4 where the sulfonic acid has an alkyl group of from 12 to 40 carbon atoms.

7. The product obtained by the process of claim 1.

8. A salt formed by contacting the product of claim 7 with an alkali metal compound, an alkaline earth metal compound, or a quarternary nitrogen compound.

9. The salt of claim 8 where the alkali metal is lithium, potassium, or sodium and the alkaline earth metal is calcium, magnesium, or barium.

10. The product of claim 8 that is overbased.

11. A sulfonic acid or sulfonate salt containing at least 1% by weight based on the weight of the sulfonic acid or sulfonate of at least one unsaturated hydrocarbon, where the unsaturated hydrocarbon is selected from at least one of (A), (B), (C) or (D), where
    (A) has at least one carbon to carbon double bond, the carbon atoms bonded by said bond being unsubstituted or being substituted with one hydrocarbyl group in total;
    (B) has at least one carbon to carbon double bond, the carbon atoms bonded by said bond being substituted with two hydrocarbyl groups in total;
    (C) bonded by said bond being substituted with three hydrocarbyl groups in total; and
    (D) has at least one carbon to carbon double bond, the carbon atoms bonded by said bond being substituted with four hydrocarbyl groups in total;
    wherein each of (A), (B), (C) and (D) has from 2 to 8 carbon atoms.

12. The sulfonic acid or sulfonate salt of claim 11 containing from 2 to 10% by weight based on the weight of the sulfonic acid or sulfonate of unsaturated hydrocarbon.

13. The sulfonic acid or sulfonate salt of claim 12 containing from 3 to 6% by weight based on the weight of the sulfonic acid or sulfonate of unsaturated hydrocarbon.

14. A lubricating oil concentrate comprising the product of claim 7 in a diluent oil or solvent.

15. A lubricating oil composition comprising a major proportion of a lubricating oil and a minor proportion, admixed therewith, of the product of claim 7.

16. The process of claim 1, wherein (C) and (D) each have from 5 to 8 carbon atoms.

17. A lubricating oil concentrate comprising the salt of claim 8 in a diluent oil or solvent.

18. A lubricating oil concentrate comprising the sulfonic acid or sulfonate salt of claim 11 in a diluent oil or solvent.

19. A lubricating oil composition comprising a major proportion of a lubricating oil and a minor proportion, admixed therewith, of a salt of claim 8.

20. A lubricating oil composition comprising a major proportion of a lubricating oil and a minor proportion, admixed therewith, of a sulfonic acid or sulfonate salt of claim 11.

21. A process for improving the odour of a sulfonic acid comprising contacting the sulfonic acid with at least one unsaturated hydrocarbon selected from at least one of (A) or (B), where (A) has at least one carbon to carbon double bond, the carbon atoms bonded by said bond being unsubstituted or being substituted with one hydrocarbyl group in total; and (B) has at least one carbon to carbon double bond, the carbon atoms bonded by said bond being substituted with two hydrocarbyl groups in total;

wherein each of (A) and (B) have from 2 to 8 carbon atoms.

* * * * *